(12) United States Patent
Karl et al.

(10) Patent No.: US 8,688,194 B2
(45) Date of Patent: Apr. 1, 2014

(54) MEDICAL IMAGING SYSTEM

(75) Inventors: Ulrich Karl, Neustadt am Kulm (DE);
Kerstin Waldbach, Porstendorf (DE);
Herbert Weiler, Alling (DE)

(73) Assignee: Siemens Aktiengesellschaft, München (DE)

( * ) Notice: Subject to any disclaimer, the term of this patent is extended or adjusted under 35 U.S.C. 154(b) by 1220 days.

(21) Appl. No.: 11/660,801

(22) PCT Filed: Aug. 16, 2005

(86) PCT No.: PCT/EP2005/054029
§ 371 (c)(1),
(2), (4) Date: Feb. 21, 2007

(87) PCT Pub. No.: WO2006/024602
PCT Pub. Date: Mar. 9, 2006

(65) Prior Publication Data
US 2007/0287908 A1    Dec. 13, 2007

(30) Foreign Application Priority Data

Sep. 1, 2004  (DE) .......................... 10 2004 042 314

(51) Int. Cl.
*A61B 5/05*    (2006.01)

(52) U.S. Cl.
USPC ........................................................ 600/415

(58) Field of Classification Search
USPC ............................................. 600/415; 5/601
See application file for complete search history.

(56) References Cited

U.S. PATENT DOCUMENTS

| 5,014,292 | A | | 5/1991 | Siczek et al. |
|---|---|---|---|---|
| 5,499,415 | A | * | 3/1996 | McKenna ......................... 5/601 |
| 6,045,262 | A | * | 4/2000 | Igeta et al. .................... 378/209 |
| 6,152,598 | A | | 11/2000 | Tomisaki et al. |
| 2001/0047543 | A1 | * | 12/2001 | VanSteenburg et al. ..... 5/81.1 C |
| 2004/0143177 | A1 | * | 7/2004 | Falbo et al. ................... 600/407 |

FOREIGN PATENT DOCUMENTS

| DE | 197 36 884 A1 | | 3/1999 |
|---|---|---|---|
| EP | 1400202 | * | 6/2002 |
| EP | 1 400 202 A1 | | 3/2004 |
| EP | 1400202 A1 | * | 3/2004 |
| JP | 9-266893 | | 10/1997 |
| JP | 09266893 | | 10/1997 |
| JP | 2001-128955 | | 5/2001 |
| JP | 2001128955 | | 5/2001 |

OTHER PUBLICATIONS

Magnetom Concerto—Open to everyone published by Siemens AG (ordering No. A91100-M2220-A554-1-7600 and available at the time of application at www.siemensMedical.com).
German Office Action dated Apr. 20, 2005 for DE 10 2004 042 314.8-35 and translation.
International Search Report for PCT/EP2005/054029, May 4, 2007.

* cited by examiner

*Primary Examiner* — Tse Chen
*Assistant Examiner* — Hien Nguyen
(74) *Attorney, Agent, or Firm* — Lempia Summerfield Katz LLC

(57) ABSTRACT

A medical imaging system is provided. The medical imaging system includes a patient positioning table and a patient examination area that is open on at least three sides and accessible from a front side. The patient positioning table is able to be moved into the patient examination area. At least one positioning motor is arranged on a rear side and is separated from the front side by a rear wall element. The at least one positioning motor is operable to adjust the position of a framework. The patient positioning table is disposed on the framework.

18 Claims, 3 Drawing Sheets

MEDICAL IMAGING SYSTEM

The present patent document is a §371 continuation of PCT Application Serial Number PCT/EP2005/054029, filed Aug. 16, 2005, designating the United States, which is hereby incorporated by reference. This patent document also claims the benefit of DE 10 2004 042 314.8, filed Sep. 1, 2004.

BACKGROUND

The present embodiments relate to an apparatus for producing medical images or for therapy.

In an apparatus for producing medical images (medical imaging system) or for therapy, for example, in computerized tomography (CT) or magnetic resonance (MR) systems, a patient positioning table is used to place the patients to be examined into an examination area or an imaging volume of the medical apparatus. Generally, the patient is moved within the examination area in a defined manner so that a specific volume of the body can be examined. The apparatus is embodied in part as a closed system in which the patient positioning table is moved into or through a tube. An open system includes an examination patient is open on at least three sides. In an open magnetic resonance system, the area that moved in between an upper coil section and a lower coil section. An open magnetic resonance system of this type is described in, for example, the brochure "Magnetom Concerto—Open to everyone" published by Siemens AG (ordering number A91100-M2220-A554-1-7600 and available at the time of application at www.siemensMedical.com).

In an open system of this type, the patient is moved into the examination area from the front or side by the patient positioning table. The patient positioning table should restrict access to the examination area as little as possible, should be easy to operate, and should furthermore enable the patient to be positioned in a defined manner.

SUMMARY

The present embodiments may obviate one or more of the drawbacks or limitations inherent in the related art. An apparatus for producing medical images restricts access to as little of the examination area as possible, is easy to operate, and enables the patient to be positioned in a defined manner.

In one embodiment, an apparatus for producing medical images or for therapy includes a patient positioning table and a patient examination area that is open on at least three sides and accessible from a front side. The patient positioning table can be moved into the patient examination area. The patient positioning table is arranged on a framework whose position can be adjusted by a motor, in particular an electric motor. At least one positioning motor arranged on a rear side turned away from the front side by a rear wall element is therein provided for adjusting the position of the framework.

In one embodiment, an electric motor enables the patient positioning table to be operated and adjusted conveniently and easily. In open systems, the apparatus has a roughly C-shaped housing with a lower section and an upper section connected to each other on their rear side via the rear wall element. In one embodiment, at least one positioning motor is arranged on the rear wall element's rear side facing away from the patient positioning table. The front area does not include bulky positioning motors. The front area should be as freely accessible as possible. The positioning motors are arranged optically behind the rear wall element.

A magnetic resonance system has the positioning motor(s) separated by the rear wall element from the magnetic field produced by the coils of the magnetic resonance system. The disruptions to image recording emanating from the electric motor can be substantially eliminated using, for example, a suitable structure.

A patient positioning table is adjusted by an electromotive device. The customary plurality of positioning motors are arranged behind the rear wall element and the necessary adjustment forces to the patient positioning table are transmitted via, in particular, mechanical force transmitting elements.

In one embodiment, the framework is open on the front side, which is in front of the examination area, and has a U-shaped supporting frame running laterally from the rear side toward the front side. The framework has no transverse component on the front side. The examination area remains freely accessible from the front. The U-shaped supporting frame provides sufficiently good stability.

In one embodiment, the framework is cantilevered and does not have base supports, at least in the area of the front side. Only laterally running arms of the supporting frame are arranged in the device's front area. The patient positioning table is supported by the laterally running arms. The front area should be as freely accessible as possible.

In one embodiment, the framework is connected to the rear wall element. The framework is an integral part of the magnetic resonance system. The patient positioning table cannot be moved freely and independently of the magnetic resonance system.

In one embodiment, the at least one positioning motor is arranged in a fixed and stationary manner. The positioning motor does not participate in the framework's motion. The magnetic fields produced by the electric motor are stationary and insofar "static." The influence of the positioning motors on the magnetic resonance system's magnetic examination field is largely constant. Possible interference effects of the electric motors can be simply compensated by a suitable structure, for instance, the placement of shim plates. Shim plates serve as correcting plates for homogenizing the magnetic field produced by the magnetic resonance system.

In one embodiment, the position of the patient positioning table can be adjusted in three directions, specifically in the longitudinal direction, in the transverse direction, and in height. A separate, in particular stationary, positioning motor is provided for each direction. The use of one positioning motor for each individual degree of freedom allows the position of the patient positioning table to be adjusted in each of the three directions mutually independently.

For adjusting the patient positioning table in the longitudinal direction, which is the direction from the rear side toward the front side, the framework expediently has a rail that is extendable in the longitudinal direction. The rail runs on or in the supporting frame's arms and is embodied such that the patient positioning table arranged on said rail can be moved forward in the longitudinal direction out of or into the examination area. The supporting frame's arm does not protrude beyond the front side of the apparatus. Only the rail in its extended condition extends beyond the lower section of the apparatus. The rail can be extended sufficiently far for the patient positioning table to be height-adjustable in front of the lower section of the apparatus. The patient positioning table can be lowered in front of the lower section of the apparatus sufficiently far for a patient to be able to sit comfortably on the table without having to mount a step, stairs, or ladder. After the patient has sat or laid in position, the table can again be raised above the lower section of the apparatus and moved into the examination area.

In one embodiment, the patient positioning table is able to be adjusted in a direction transverse to the longitudinal direction. The adjustability by the positioning motor serves to move the patient in a defined manner through the evaluation or examination volume of the magnetic resonance system. A drive shaft extends forward from the positioning motor located on the rear side into the area of the patient positioning table. The drive shaft adjusts the patient positioning table in the transverse direction. The turning motion of the drive shaft is transmitted via a coupling element, in particular a driving belt, to the patient positioning table to move it transversally. The coupling element is embodied in such a way that it will be compliantly moved in the longitudinal direction when the patient positioning table is moved longitudinally. The drive shaft is fixed, and the coupling element is movable on the shaft. In an alternative embodiment, the coupling element is permanently connected to the drive shaft and the drive shaft being movable or extendable in the longitudinal direction. In one embodiment, as regards the third degree of freedom, namely height adjusting the patient positioning table, a vertical guiding device for the supporting frame is provided on the rear wall element.

DETAILED DESCRIPTION

Figure 1:
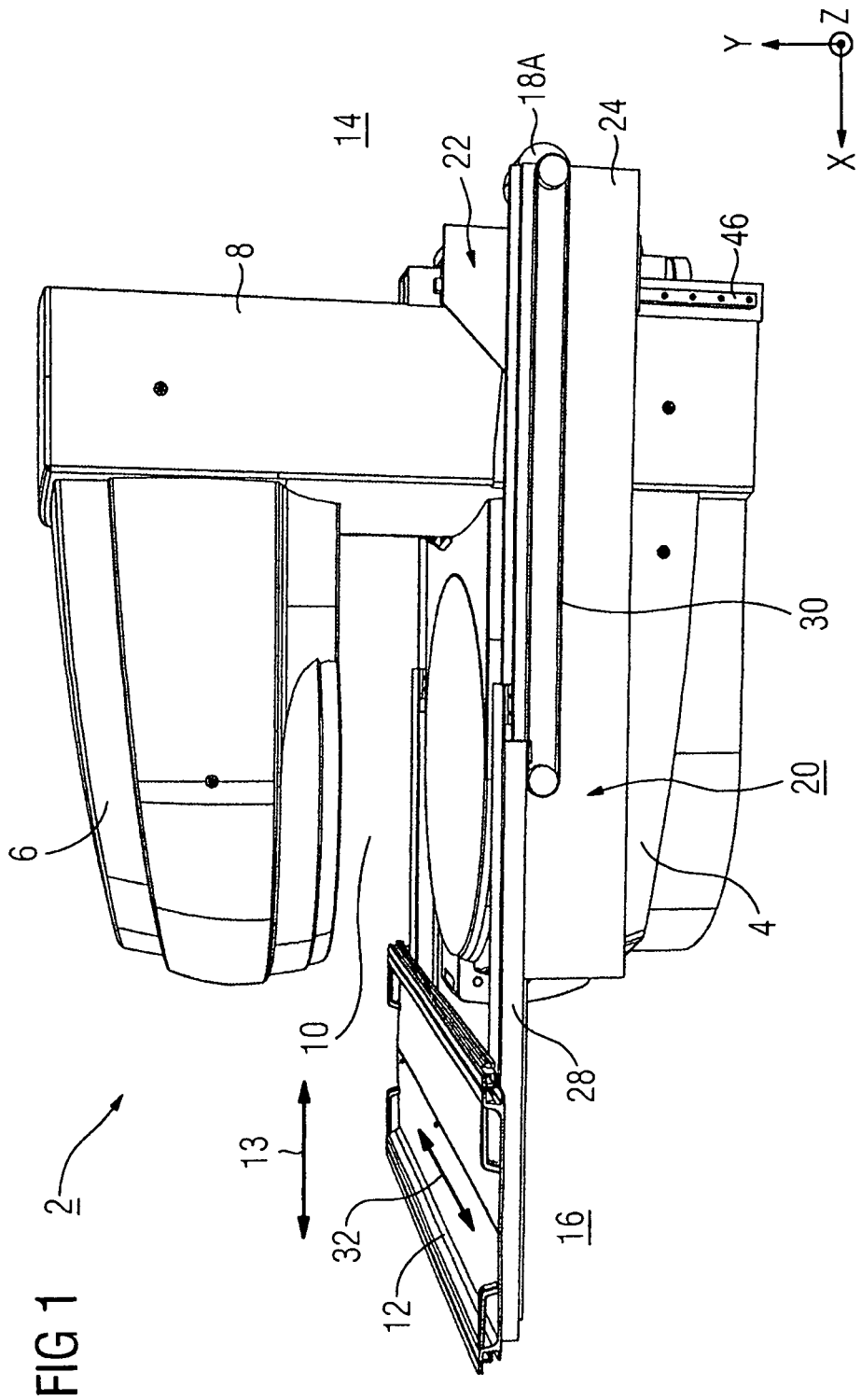
FIG. 1 is a side view of one embodiment of an open magnetic resonance system having an integrated patient positioning table extended in the longitudinal direction.

The same parts have been assigned the same reference numerals in the figures.

In one embodiment, the magnetic resonance system 2 is an open system and is roughly C-shaped in design. The system 2 includes a lower section 4 and an upper section 6 that are connected to each other via a rear wall element 8. The lower and upper sections 4, 6 each contain a magnet coil. Located between the lower and upper sections 4, 6 is an examination area 10 into which a patient is moved to be examined. The examination area 10 is referred to as the imaging volume. A defined magnetic field is produced within the imaging volume or area by the coils. The defined magnetic field is used for examining based on the evaluation of the magnetic resonance. Imaging is used for the evaluation.

The patient is moved into the examination area 10 on a patient positioning table 12. The open magnetic resonance system 2 includes an examination area 10 that is overall accessible from at least three sides, specifically from the front and from the two sides. The system 2 extends in the longitudinal direction 13 (identified in the figures as the X direction) from a rear side 14 to a front side 16.

The position of the patient positioning table 12 is adjusted with three electric positioning motors 18A, B, C and mechanical force transmitting elements that transmit the positioning motions and positioning forces exerted by the positioning motors 18A, B, C to the patient positioning table 12.

The three positioning motors 18A, B, C are arranged stationarily behind the rear wall element 8, which prevents them from impeding the front area. The examination area 10 remains largely freely accessible. The magnetic interference fields emanating from the electric motors are at least partially screened by the interposed rear wall element 8. The electric motors are arranged in a fixed manner so that any residual interference fields that could disrupt the actual magnetic examination field can be eliminated by a suitable structure by stationarily disposing suitable correcting plates or correcting elements.

The system 2 includes a highly compact and space-saving framework 20 for the patient positioning table 12. The framework 20 is embodied in such a way that free front access to the examination area 10 is minimally restricted. The framework 20 includes a supporting frame 22 (major supporting element). The supporting frame 22 includes two lateral support arms 24 connected to each other on the rear side 14 via a rear-side transverse support 26. The supporting frame 22 is embodied in the shape of a U, with the opening toward the front side 16. The support arms 24 do not, or only slightly, project beyond the lower section 4 in the longitudinal direction 13.

An extendable rail 28 on which the patient positioning table 12 is secured is provided on each support arm 24. The first positioning motor 18A is provided for moving the patient positioning table 12 in the longitudinal direction. In the exemplary embodiment, the motor's 18A positioning motion is transmitted to the extendable rail 28 via a first belt drive 30.

Figure 2:
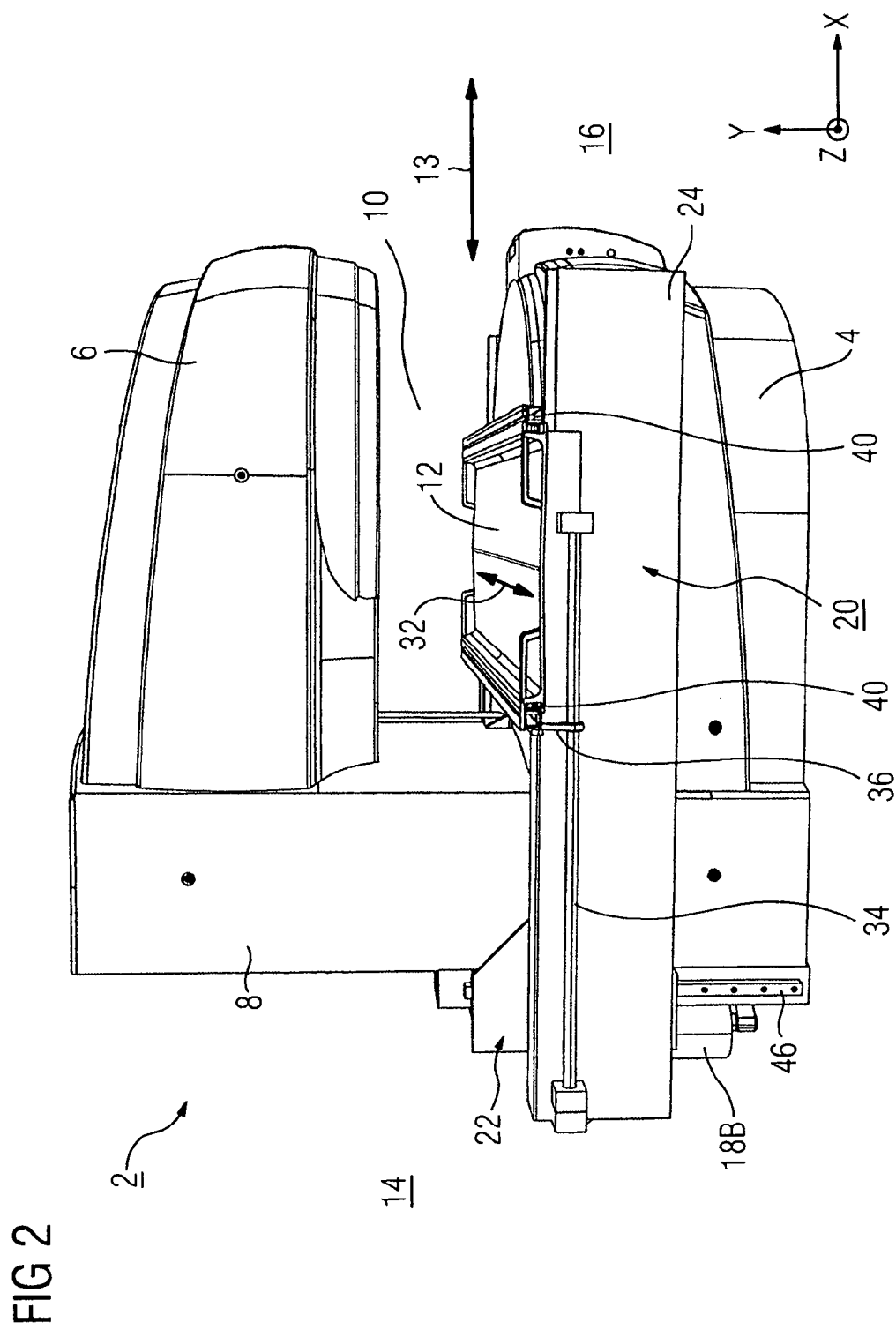
FIG. 2 is another side view of one embodiment of the magnetic resonance system shown in FIG. 1, with the patient positioning table retracted in the longitudinal direction.
Figure 3:
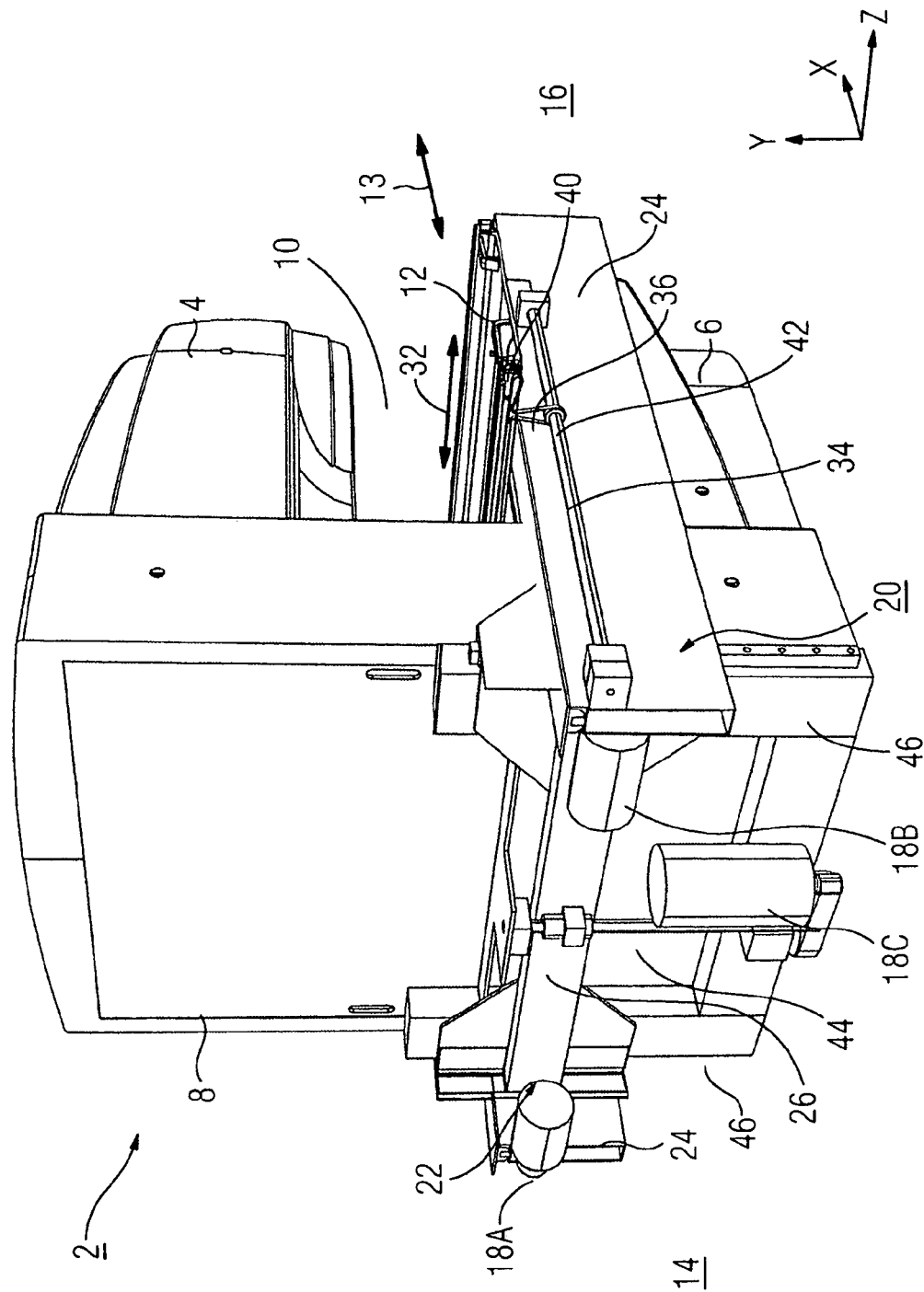
FIG. 3 is a perspective view of one embodiment of the magnetic resonance system shown in FIG. 1 and FIG. 2.

The second positioning motor 18B is provided for moving the patient positioning table 12 in the transverse direction 32. The transverse direction 32 is oriented perpendicularly to the longitudinal direction 13 and is shown in FIGS. 1-3 as the Z direction. The positioning motion of the second positioning motor 18B is transmitted via a drive shaft 34 that extends approximately up to the examination area 10. The drive shaft 34 is ducted laterally alongside one of the two support arms 24. A second belt drive 36 that includes a driving belt running around the drive shaft 34 is connected to the drive shaft 34. The driving belt produces a transverse motion of the patient positioning table 12 that is guided in a further rail system 40. The drive belt runs around a drive wheel 42 located on the drive shaft 34. The drive wheel 42 is compliantly moved in the longitudinal direction 13 when there is a positional adjustment in the longitudinal direction 13. In one embodiment, the drive wheel 42 is arranged movably in the longitudinal direction 13 on the drive shaft 34. In an alternative embodiment, the drive wheel 42 is fixed in position, and the drive shaft 34 is variable in length in the manner of, for example, a telescope tube.

The third positioning motor 18C is provided for adjusting the height of the patient positioning table 12. The third positioning motor 18C, for example, acts indirectly or directly on the transverse support 26 via a spindle drive 44 so that the force that adjusts the height is transmitted to the lateral support arms 24. To enable height adjustment, the supporting frame 22 is guided in two vertical guide elements 46 likewise arranged in the manner of arms directly on the rear wall element 8.

In one embodiment, the supporting frame 22 is supported exclusively on the guide elements 46. No further support elements are provided in, for example, the front area. The mechanical forces are transmitted to the guide elements 46 via the supporting frame 22. Because said elements are secured to the rear wall element 8, the supporting forces are designed into the overall structure of the magnetic resonance system 2.

The open magnetic resonance system 2 described here includes a patient positioning table 12 whose position can be adjusted in three directions by three positioning motors 18A, B, C. The three positioning motors 18A, B, C are located in a space-saving and minimally disruptive manner behind the rear wall element 8. The three positioning motors 18A, B, C adjust the position of the a patient positioning table 12 by electromotive means. The framework 20 supports the patient positioning table 12. The framework 20 is cantilevered and open toward the front so that access to the examination area 10 from the front side 14 is not adversely affected by the framework 20.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A medical imaging system extending in a longitudinal direction from a front side to a rear side, the medical imaging system comprising:
   a patient positioning table;
   a patient examination area that is open on at least three sides and accessible from the front side, the patient positioning table operable to be moved into the patient examination area;
   a magnetic coil that produces a magnetic field within the patient examination area; and
   at least one positioning motor that is arranged in the longitudinal direction on the rear side behind a rear wall element and is separated from the front side by the rear wall element, the at least one positioning motor being operable to adjust a position of a framework, the framework comprising two lateral support arms,
   wherein the patient positioning table is slidably attached to the two lateral support arms of the framework, and the framework is slidably attached directly to the rear wall element,
   wherein a position of the patient positioning table is adjustable in a transverse direction by the at least one positioning motor, the transverse direction being transverse to the longitudinal direction,
   wherein a drive shaft extends from the at least one positioning motor behind the rear wall element into an area of the patient positioning table in front of the rear wall element, a coupling element arranged in front of the rear wall element being configured to transmit a turning motion of the drive shaft such that the patient positioning table moves in the transverse direction,
   wherein at least three positioning motors are arranged on the rear side and are separated from the front side, the at least three positioning motors including the at least one positioning motor, the at least three positioning motors being operable to position the patient positioning table in three directions, and
   wherein the position of the patient positioning table is adjustable in the longitudinal direction from the rear side toward the front side, and wherein the framework includes a rail that is extendable in the longitudinal direction so that the patient positioning table is movable in the longitudinal direction into or out of the examination area.

2. The medical imaging system as claimed in claimed 1, wherein the framework is open on the front side in front of the examination area and includes a U-shaped supporting frame that extends laterally from the rear side toward the front side.

3. The medical imaging system as claimed in claim 1, wherein the framework is cantilevered without base supports in the area of the front side.

4. The medical imaging system as claimed in claim 1, wherein the at least one positioning motor is in a stationary position.

5. The medical imaging system as claimed in claimed 1, wherein a vertical guide element that is arranged on the rear wall element is operable to adjust the height of the patient positioning table.

6. The medical imaging system as claimed in claim 1, wherein the at least one positioning motor is separated from the front side by the rear wall element.

7. The medical imaging system as claimed in claim 2, wherein the framework is cantilevered without base supports in the area of the front side.

8. The medical imaging system as claimed in claim 1, wherein one of the at least three positioning motors is provided for each direction.

9. The medical imaging system as claimed in claim 1, wherein the three directions include the longitudinal direction, the transverse direction, and a height direction.

10. The medical imaging system as claimed in claim 1, wherein the drive shaft is ducted.

11. A magnetic resonance system extending in a longitudinal direction from a front side to a rear side, the magnetic resonance system comprising:
    a patient positioning table disposed on a framework, the framework comprising two lateral support arms;
    a patient examination area open on at least three sides and accessible from the front side, the patient positioning table operable to be moved into the patient examination area;
    an upper coil section disposed above the patient examination area and a lower coil section disposed below the patient examination area;
    a rear structure between the upper coil section and the lower coil section, the rear structure opposite the front side relative to the patient examination area;
    at least one positioning motor that is arranged in the longitudinal direction on the rear side behind the rear structure and is separated from the front side by the rear structure, the at least one positioning motor being operable to adjust a position of the framework,
    wherein the patient positioning table is slidably attached directly to the two lateral support arms of the framework, and the framework is slidably attached to the rear structure,
    wherein a position of the patient positioning table is adjustable in a transverse direction by the at least one positioning motor, the transverse direction being transverse to the longitudinal direction,
    wherein a drive shaft extends from the at least one positioning motor behind the rear structure into the area of the patient positioning table in front of the rear structure, a coupling element arranged in front of the rear structure being configured to transmit turning motion of the drive shaft such that the patient positioning table moves in the transverse direction,
    wherein at least three positioning motors are arranged on the rear side and are separated from the front side, the at least three positioning motors including the at least one positioning motor, the at least three positioning motors being operable to position the patient positioning table in three directions, and
    wherein the position of the patient positioning table is adjustable in the longitudinal direction from the rear side toward the front side, and wherein the framework includes a rail that is extendable in the longitudinal direction so that the patient positioning table is movable in the longitudinal direction into or out of the examination area.

12. The medical imaging system as claimed in claim 1, wherein the turning motion of the drive shaft is transmitted via a driving belt such that the patient positioning table moves in the transverse direction.

13. The magnetic resonance system as claimed in claim 11, wherein the turning motion of the drive shaft is transmitted via a driving belt such that the patient positioning table moves in the transverse direction.

14. The magnetic resonance system as claimed in claim 11, wherein the framework comprises a U-shaped supporting frame having the two lateral support arms.

15. The magnetic resonance system as claimed in claim 11, wherein the drive shaft is ducted laterally alongside one of the two lateral support arms.

16. The magnetic resonance system as claimed in claim 13, wherein the driving belt is connected to the drive shaft, the driving belt producing the transverse motion via a drive wheel located on the drive shaft.

17. A medical imaging system extending in a longitudinal direction from a front side to a rear side, the medical imaging system comprising:
    a patient positioning table;
    a patient examination area that is open on at least three sides and accessible from the front side, the patient positioning table operable to be moved into the patient examination area;
    a magnetic coil that produces a magnetic field within the patient examination area; and
    at least one positioning motor that is arranged in the longitudinal direction on the rear side behind a rear wall element and is separated from the front side by the rear wall element, the at least one positioning motor being operable to adjust a position of a framework, the framework comprising two lateral support arms,
    wherein the patient positioning table is slidably attached to the two lateral support arms of the framework, and the framework is slidably attached directly to the rear wall element,
    wherein a position of the patient positioning table is adjustable in a transverse direction by the at least one positioning motor, the transverse direction being transverse to the longitudinal direction,
    wherein a drive shaft extends from the at least one positioning motor behind the rear wall element into an area of the patient positioning table in front of the rear wall element, a coupling element arranged in front of the rear wall element being configured to transmit a turning motion of the drive shaft such that the patient positioning table moves in the transverse direction,
    wherein at least three positioning motors are arranged on the rear side and are separated from the front side, the at least three positioning motors including the at least one positioning motor, the at least three positioning motors being operable to position the patient positioning table in three directions,
    wherein the position of the patient positioning table is adjustable in the longitudinal direction from the rear side toward the front side, and wherein the framework includes a rail that is extendable in the longitudinal direction so that the patient positioning table is movable in the longitudinal direction into or out of the examination area, and
    wherein one positioning motor of the at least three positioning motors is provided for each of the three directions.

18. A magnetic resonance system extending in a longitudinal direction from a front side to a rear side, the magnetic resonance system comprising:
    a patient positioning table disposed on a framework, the framework comprising two lateral support arms;
    a patient examination area open on at least three sides and accessible from the front side, the patient positioning table operable to be moved into the patient examination area;
    an upper coil section disposed above the patient examination area and a lower coil section disposed below the patient examination area;
    a rear structure between the upper coil section and lower coil section, the rear structure being opposite the front side relative to the patient examination area;
    at least one positioning motor that is arranged in the longitudinal direction on the rear side behind the rear structure and is separated from the front side by the rear structure, the at least one positioning motor being operable to adjust a position of the framework,
    wherein the patient positioning table is slidably attached directly to the two lateral support arms of the framework, and the framework is slidably attached to the rear structure,
    wherein a position of the patient positioning table is adjustable in a transverse direction by the at least one positioning motor, the transverse direction being transverse to the longitudinal direction,
    wherein a drive shaft extends from the at least one positioning motor behind the rear structure into an area of the patient positioning table in front of the rear structure, a coupling element arranged in front of the rear structure being configured to transmit a turning motion of the drive shaft such that the patient positioning table moves in the transverse direction,
    wherein the framework is connected to the rear structure,
    wherein the framework comprises a U-shaped supporting frame having the two lateral support arms,
    wherein the drive shaft is ducted laterally alongside one of the two support arms,
    wherein at least three positioning motors are arranged on the rear side and are separated from the front side, the at least three positioning motors including the at least one positioning motor, the at least three positioning motors being operable to position the patient positioning table in three directions, and
    wherein the position of the patient positioning table is adjustable in the longitudinal direction from the rear side toward the front side, and wherein the framework includes a rail that is extendable in the longitudinal direction so that the patient positioning table is movable in the longitudinal direction into or out of the examination area.

* * * * *